United States Patent [19]

Brenner et al.

[11] 4,055,634
[45] Oct. 25, 1977

[54] ANTIPERSPIRANTS

[75] Inventors: Wolf Brenner, Fullinsdorf; Gustav Erlemann, Basel; Horst Pauling, Bottmingen, all of Switzerland

[73] Assignee: Hoffmann-La Roche, Inc., Nutley, N.J.

[21] Appl. No.: 549,241

[22] Filed: Feb. 11, 1975

[30] Foreign Application Priority Data

Feb. 22, 1974 Switzerland .................. 2538/74
Dec. 3, 1974 Switzerland ................ 16014/74

[51] Int. Cl.² .................... A61K 7/38; C07F 5/06
[52] U.S. Cl. .......................... 424/47; 260/448 A; 260/448 AD; 424/68
[58] Field of Search ............ 260/448 AD, 448 A; 424/47, 68

[56] References Cited

U.S. PATENT DOCUMENTS

| | | | |
|---|---|---|---|
| 2,872,379 | 2/1959 | Neumann | 424/47 |
| 2,892,858 | 6/1959 | Ziegler | 260/448 AD |
| 3,030,274 | 4/1962 | Grant | 424/47 |
| 3,294,770 | 12/1966 | Ragazzini et al. | 260/448 AD |
| 3,318,934 | 5/1967 | Hoffmann et al. | 260/448 AD |
| 3,381,024 | 4/1968 | Toyoshima et al. | 260/448 AD |
| 3,444,226 | 5/1969 | Schmank et al. | 260/448 |
| 3,444,292 | 5/1969 | Beckman et al. | 424/58 |
| 3,448,189 | 6/1969 | Icken et al. | 424/74 |
| 3,488,370 | 6/1970 | Leary et al. | 260/448 |
| 3,509,253 | 4/1970 | Babbin | 424/47 |

FOREIGN PATENT DOCUMENTS

| | | | |
|---|---|---|---|
| 1,162,369 | 2/1964 | Germany | |
| 1,767,875 | 9/1971 | Germany | 424/68 |
| 1,467,949 | 10/1969 | Germany | 424/68 |
| 1,005,690 | 9/1957 | Germany | 424/47 |
| 276,920 | 10/1964 | Netherlands | |
| 107,669 | 10/1965 | Norway | 424/68 |
| 1,150,845 | 5/1969 | United Kingdom | 424/47 |
| 799,823 | 8/1958 | United Kingdom | 424/78 |
| 751,516 | 6/1956 | United Kingdom | 424/68 |
| 1,024,501 | 3/1966 | United Kingdom | |

OTHER PUBLICATIONS

Walker Serfen-Ole-Fette-Wachse, 1966, vol. 92, No. 24; pp. 882-883.
Lehmkuhl et al., Liebegs, Amer. Chem. 1967, vol. 705, pp. 23-31.
Storr et al., JACS, 1968, vol. 90, pp. 3173-3177.
Grosse et al., J. Org. Chem., 1940, vol. 5, pp. 106-121.
Ziegler et al., Annelen Der. Cheme, 1960, vol. 629, pp. 251-256.
Muller Journ. of Org. Metallic Chem., 1968, vol. 14, pp. 253-259.
Fiedler Der Schweiss, 1968, pp. 323, 337, 373.

Primary Examiner—Dale R. Ore
Attorney, Agent, or Firm—Samuel L. Welt; Bernard S. Leon; R. Hain Swope

[57] ABSTRACT

Compounds represented by the formula

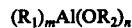

$(R_1)_m Al(OR_2)_n$       I wherein $m$ and $n$ each are 1 or 2 and the sum of $m$ and $n$ is 3; $R_1$ is alkyl; $R_2$ is substituted and unsubstituted alkyl, cycloalkyl, alkenyl, cycloalkenyl, aryl, alkanoyl, alkenoyl or aroyl; wherein the substituents on $R_2$ when $R_2$ is alkyl, alkenyl, alkanoyl and alkenoyl are one or more of cycloalkyl, cycloalkenyl, alkyl substituted cycloalkenyl, or aryl, alkoxy, cycloalkoxy, cycloalkenyloxy, aryloxy or alkyl and/or alkoxy substituted aryl, alkoxy, cycloalkoxy, cycloalkenyloxy or aryloxy; and wherein the substituents on $R_2$ when $R_2$ is cycloalkyl, cycloalkenyl, aryl and aroyl are one or more of alkyl, alkoxy or aryl; and when $R_2$ is phenyl two adjacent alkyl and/or alkoxy substituents on the phenyl can be joined to form a 5 or 6-membered saturated ring; when $m$ is 2 and $n$ is 1, $R_2$ can be

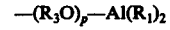

$-(R_3O)_p-Al(R_1)_2$       (a)

wherein $R_1$ has the significance above and each $R_1$ can be the same or different, $R_3$ is a straight chain alkylene of 2 to 4 carbons and $p$ is 0, 1 or 2; when $m$ is 1 and $n$ is 2, $R_2$ has the significance above and each $R_2$ can be the same or different or when one $R_2$ is alkyl the other $R_2$ can be

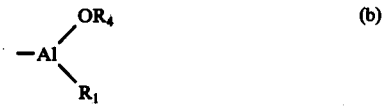

wherein $R_1$ has the significance above and $R_4$ is alkyl; are disclosed as having activity as antiperspirants.

Antiperspirant/deodorant compositions containing one or more of the compounds as active ingredients and methods for preparing the compounds are also disclosed.

14 Claims, No Drawings

ANTIPERSPIRANTS

DESCRIPTION OF THE INVENTION

This invention provides compounds, some heretofore known and some novel, which have activity as antiperspirants. The active compounds are represented by the following formula

$$(R_1)_m Al(OR_2)_n \qquad I$$

wherein $m$ and $n$ each are 1 or 2 and the sum of $m$ and $n$ is 3; $R_1$ is alkyl; $R_2$ is substituted and unsubstituted alkyl, cycloalkyl, alkenyl, cycloalkenyl, aryl, alkanoyl, alkenoyl or aroyl; wherein the substituents on $R_2$ when $R_2$ is alkyl, alkenyl, alkanoyl and alkenoyl are one or more of cycloalkyl, cycloalkenyl, alkyl substituted cycloalkenyl, or aryl, alkoxy, cycloalkoxy, cycloalkenyloxy, aryloxy or alkyl and/or alkoxy substituted aryl, alkoxy, cycloalkoxy, cycloalkenyloxy or aryloxy; and wherein the substituents on $R_2$ when $R_2$ is cycloalkyl, cycloalkenyl, aryl and aroyl are one or more of alkyl, alkoxy or aryl; and when $R_2$ is phenyl two adjacent alkyl and/or alkoxy substituents on the phenyl can be joined to form a 5 or 6-membered saturated ring; when $m$ is 2 and $n$ is 1, $R_2$ can be $$-(R_3O)_{p'}-Al(R_1)_2 \qquad (a)$$

wherein $R_1$ has the significance above and each $R_1$ can be the same or different, $R_3$ is a straight chain alkylene of 2 to 4 carbons and $p$ is 0, 1 or 2; when $m$ is 1 and $n$ is 2, $R_2$ has the significance above and each $R_2$ can be the same or different or when one $R_2$ is alkyl the other $R_2$ can be

(b)

wherein $R_1$ has the significance above and $R_4$ is alkyl.

The active compounds of this invention which are novel are represented by the following formula $$(R_1)_m Al(OR_{20})_n \qquad I(c)$$

wherein $m$ and $n$ each are a number from 1 to 2 and sum of $m$ and $n$ is 3; $R_1$ is alkyl; $R_{20}$ is one or more of an alkyl containing from 14 to 30 carbons, cyclopentyl, an alkenyl containing from 7 to 30 carbons, a cycloalkenyl, a naphthyl, an alkenoyl containing from 5 to 30 carbons, a naphthoyl, an alkyl substituted by one or more of cycloalkyl, cycloalkenyl, alkyl-substituted cycloalkenyl, alkyl- and/or alkoxy-substituted aryl, cycloalkoxy, cycloalkenyloxy or aryloxy; an alkenyl, alkanoyl or alkenoyl substituted by cycloalkyl, cycloalkenyl, alkyl-substituted cycloalkenyl, aryl, alkoxy, cycloalkoxy, cycloalkenyloxy, aryloxy or by alkyl and/or alkoxy-substituted aryl, alkoxy, cycloalkoxy, cycloalkenyloxy or aryloxy; a cycloalkyl, cycloalkenyl, aryl or aroyl substituted by alkoxy and/or aryl; or a cycloalkyl, cycloalkenyl, aryl or aroyl substituted by alkoxy and/or aryl and additionally by alkyl; or phenyl substituted by alkyl and/or alkoxy wherein two adjacent alkyl and/or alkoxy substituents are joined to form a 5- or 6-membered saturated ring; when $m$ is 2 and $n$ is 1, $R_{20}$ can also be $$-Al(R_{10})_2 \qquad (a')$$

wherein $R_1$ and $R_{10}$ are alkyl containing from 10 to 30 carbons; when $m$ is 2 and $n$ is 1 $R_{20}$ can be $$-(R_3O)_{p'}-Al(R_{11})_2 \qquad (a'')$$

wherein $R_1$ and $R_{11}$ are alkyl containing from 2 to 30 carbons, $R_3$ is a straight chain alkylene containing 2 to 4 carbons and p' is 1 or 2; or when $m$ is 1 and $n$ is 2, $R_{20}$ has the significance above and each $R_{20}$ can be the same or different or when one of $R_{20}$ is an alkyl containing from 3 to 30 carbons the other can be

(b')

where $R_1$ has the significance given above and $R_{40}$ is an alkyl containing from 3 to 30 carbons.

The meanings and scope of the terms used to define $n$, $m$, $R_1$ and $R_{20}$ in formula Ic is — within the scope of the definition given in formula Ia — the same as described in detail hereinafter for $n$, $m$, $R_1$ and $R_2$ in formula I.

Among the novel compounds within the scope of formula Ic which are suitable for use in this invention are those in which $R_{20}$ is an alkyl substituted by cycloalkyl, cycloalkoxy or aryloxy; an alkenyl substituted by alkyl-substituted cycloalkenyl or alkoxy; an alkenoyl substituted by alkyl-substituted cycloalkenyl or by alkyl- and/or alkoxy-substituted aryl; or an alkyl-substituted chromanyl. Preferred compounds are those in which $R_1$ is a alkyl containing 2 to 8 carbons and $R_{20}$ is a phenoxyalkyl containing 7 to 14 carbons.

The alkyl, alkoxy, alkenyl, alkanoyl and alkenoyl substituents in the compounds of formula I can be straight-chain or branched-chain and contain from 1 to 30 carbons, preferably 1 to 20 carbons. Especially preferred are alkyl, alkoxy, alkenyl, alkanoyl and alkenoyl containing 1 to 8 carbons. Alkyl groups represented by $R_1$ preferably contain from 2 to 30 carbons. Examples of alkyls denoted by $R_1$ or $R_2$ and also present in the alkoxy substituent are methyl, ethyl, n-propyl, isopropyl, n-butyl, isobutyl, sec. butyl, tert. butyl, n-pentyl, isopentyl, neopentyl, n-hexyl, n-decyl, n-undecyl, n-dodecyl, n-tetradecyl, n-hexadecyl, n-octadecyl, n-eicosyl and n-triacontyl. Examples of alkenyls denoted by $R_2$ are vinyl, allyl, but-2-enyl, penta-2,4-dienyl, geranyl, nerolyl, phytyl and 3,7-dimethyl-octa-2,6-dien-1-yl. The alkanoyls denoted by $R_2$ contain from 2 to 30 carbons. Examples of such alkanoyls are acetyl, propionyl, n-butyryl, isobutyryl, pivaloyl, n-pentanoyl, n-hexanoyl, n-octanoyl, n-decanoyl, n-undecanoyl, n-dodecanoyl, n-tetradecanoyl, n-hexadecanoyl, n-octadecanoyl, n-eicosanoyl, n-triacontanoyl. Examples of alkenoyls denoted by $R_2$ are acryloyl, but-2-enoyl (crotonyl), penta 2,4-dienoyl, hexa-2,4-dienoyl (sorbyl), undec-10enoyl, geranoyl, octadec-9-enoyl (oleoyl), octadeca-9,12-dienoyl (linolyl), octadeca-9,12,15-trienoyl (linolenyl) and eicos-5-enoyl.

Cycloalkyl and cycloalkenyls denoted by $R_2$ preferably contain 5 or 6 carbons, e.g., cyclopentyl, cyclohexyl, cyclopentenyl and cyclohexenyl.

The term "aryl" as used herein alone or in connection with "aryloxy" or "aroyl" means an aromatic, mononuclear or polynuclear hydrocarbon such as, for example, phenyl, naphthyl and phenanthryl. The terms "aryloxy" or "aroyl" as used herein mean an aryl-O- or aryl-CO- respectively. Examples of aryloxy and aroyl are phenoxy, naphthyloxy, phenanthryloxy, and benzoyl, naphthoyl and phenanthroyl. Preferred aryl, aryloxy and aroyls are those having 1 or 2 aromatic nuclei.

Examples of additional substituents on the above $R_2$ substituents are:

cycloalkyl-alkyl, e.g., cyclohexylmethyl and cyclopentylethyl;

cycloalkyl-alkenyl, e.g., cyclohexylallyl;

cycloalkyl-alkanoyl, e.g., cyclopropylacetyl and cyclohexylacetyl;

cycloalkyl-alkenoyl, e.g., cyclohexylhexa-2,4-dienoyl;

alkenyl substituted by alkyl-substituted cycloalkenyl, e.g., retinyl, such as all-trans-retinyl;

alkenoyl substituted by alkyl-substituted cycloalkenyl, e.g., retinoyl, such as all-trans-retinoyl;

alkyl substituted by alkyl- and/or alkoxy-substituted aryl, e.g., benzyl, phenethyl, naphthylmethyl, p-tolymethyl, p-methoxypenylethyl and p-methoxy-o-methyl-phenylmethyl;

alkenyl substituted by alkyl- and/or alkoxy-substituted aryl, e.g., styryl, cinnamyl, p-methylstyryl and o-methoxy-p-methylcinnamyl;

alkanoyl substituted by alkyl- and/or alkoxy-substituted aryl, e.g., phenacetyl, tolylacetyl and p-methoxyphenylacetyl;

alkenoyl substituted by alkyl- and/or alkoxy-substituted aryl, e.g., cinnamoyl, m-methoxycinnamoyl and 9-(4-methoxy-2,3,6-trimethylphenyl)-3,7-dimethyl-nona-2,4,6,8-tetraenoyl, e.g., the all-trans form;

alkoxy-alkyl, e.g., 2-methoxyethyl, ethoxymethyl and 7-methoxy-3,7-dimethyl-octyl;

alkoxy-alkenyl, e.g., 1-methoxyallyl and 7-methoxy-3,7-dimethyl-4cta-2-enyl;

alkoxy-alkanoyl, e.g., ethoxyacetyl and 3-methoxypropionyl;

alkoxy-alkenoyl, e.g., 3-methoxy-acryloyl and 6-methoxy-hexa-2,4-dienoyl (6-1 ethoxysorbyl);

cycloalkoxy-alkyl, e.g., 2-cyclohexyl-ethyl;

aryloxy-alkyl, e.g., 2-phenoxyethyl and 6-phenoxy-n-hexyl;

aryloxy-alkanoyl, e.g., phenoxyacetyl;

alkyl-cycloalkyl, e.g., 4-methyl-cyclohexyl and menthyl;

alkyl-aryl, e.g., o-, m- and p-tolyl;

alkyl-aroyl, e.g., o-, m- and p-toluoyl;

alkoxy-aryl, e.g., o-, m- and p-methoxyphenyl (anisyl);

alkoxy-aroyl, e.g., o-, m- and p-methoxybenzoyl (anisoyl);

aryl-aryl, e.g., 4-phenyl-phenyl;

aryl-aroyl, e.g., 4-phenyl-benzoyl.

As mentioned in formula I two adjacent alkyl and/or alkoxy substituents on a phenyl denoted by $R_2$ can be joined with one another to form a 5- or 6-membered saturated ring. This provides compounds of formula I in which $R_2$ is an indanyl, benzofuranyl, 1,3-benzodioxolyl, tetrahydronaphthyl, chromanyl or 1,4-benzodioxanyl which can be subtituted in the benzene nucleus by alkyl and/or alkoxy and/or in the saturated nucleus by alkyl. An example is α-tocopheryl.

In formula I, when $m$ is 2 and $n$ is 1, $R_2$ can represent formula (a) hereinbefore. These compounds are represented by the formula $$(R_1)_2\text{---AlO---}(R_3O)_p\text{---Al}(R_1)_2 \qquad \text{I(a)}$$

wherein $R_1$, $R_3$ and $p$ have the significance given earlier.

Examples of ---$(R_3O)_p$---$Al(R_1)_2$ are:

---$Al(C_2H_5)_2$

---$CH_2CH_2OAl(C_2H_5)_2$

---$CH_2CH_2OCH_2CH_2OAl(C_2H_5)_2$ and

---$CH_2CH_2 OCH_2CH_2OAl[CH_2(CH_3)_2]_2$.

Also in formula I, when $m$ is 1 and $n$ is 2, one of the symbols $R_2$ can be alkyl and the other can be formula (b) hereinbefore. These compounds are represented by the formula $$R_1-Al\begin{matrix}OR_4\\ \diagdown\\ O\quad OR_4\\ \diagdown\diagup\\ Al\\ \diagdown\\ R_1\end{matrix} \qquad \text{I(b)}$$

wherein $R_1$ and $R_4$ each are an alkyl. For example, $R_1$ can be isobutyl and $R_4$ can be ethyl or $R_1$ and $R_4$ can both be ethyl.

In formula I, when more than one $R_2$ substituent is present, such substituents are the same as, for example, in the case of isobutyl-aluminum-di(2-phenoxyetylate). The $R_2$ substituents can, however, also be different such as, for example, in the case of ethyl-aluminum-ethylate-n-propylate.

The symbols $m$ and $n$ can each be 1 or 2 but they can also, when as $R_2$ does not represent a group of formula (a) or (b), be any number between 1 and 2. The latter instance refers to the presence of a mixture of the formulae $(R_1)_2AlOR_2$ and $R_1Al(OR_2)_2$. Such mixtures can be obtained during the manufacture of the compounds of formula I. For example, the formula $[(CH_3)_2CHCH_2]_{1.5}Al(OC_2H_5)_{1.5}$ denotes that the product consists half of diisobutyl-aluminum-ethylate and half of isobutyl-aluminum-diethylate.

Typical compounds of formula I which can be present as active ingredients in the antiperspirant/deodorant compositions of this invention are those in which $R_2$ is an alkyl substituted by cycloalkyl, cycloalkoxy or aryloxy; an alkenyl substituted by alkyl-substituted cycloalkenyl or alkoxy; an alkenoyl substituted by alkyl-substituted cycloalkenyl or by alkyl- and/or alkoxy-substituted aryl; or an alkyl-substituted chromanyl.

The more preferred group of compounds of formula I which can be present as active ingredients in the antiperspirant/deodorant compositions provided by this invention are those in which $R_1$ is an alkyl containing 2 to 8 carbons and $R_2$ is a phenoxy either unsubstituted or substituted by an alkyl containing 1 to b 8 carbon atoms in the alkyl; or a cyclohexyl either unsubstituted or substituted by an alkyl containing 1 to 4 carbons. Examples of compounds falling within this group are:

diisobutyl-aluminum-2-phenoxyethylate,
di(n-hexyl)-aluminum-2-phenoxyethylate,
diethyl-aluminum-tert.butylate,
diisobutyl-aluminum-ethylate,
isobutyl-aluminum-diethylate,
diethyl-aluminum-cyclohexylate,
diethyl-aluminum-menthylate,
di(n-octyl)-aluminum-ethylate and
di(n-hexyl)-aluminum-isopropylate.

The compounds used in the antiperspirant/deodorant compositions provided by this invention impart advantageous properties to the compositions since the compounds have good perspiration absorbing capability and neither irritate the skin nor damage clothing. The active compounds impart these advantageous properties to the antiperspirant/deodorant compositions because they do not form acids upon contact with perspiration. Prior art antiperspirants having an aluminum base such as aluminum chloride, aluminum sulfate, aluminum hydroxychloride and the like form acids when coming in contact with perspiration.

The compounds within the scope of formula I are strongly hygroscopic and range in physical form from liquid to solid. Most of the compounds have a low melting point. The compounds are very viscous or vitreous in nature. Most of the compounds are soluble in inert organic solvents such as aliphatic and aromatic hydrocarbons, e.g., n-hexane, n-heptane, benzene and toluene, ethers, e.g., diethyl ether, tetrahydrofuran, dioxane, 6-acetoxy-2,4-dimethyl-1,3-dioxane and the like and esters, e.g., ethyl acetate and isopropyl myristate.

In order to demonstrate the antiperspirant activity of the compounds within the scope of formula I, typical representative compounds were tested on human volunteers under elevated thermal conditions, i.e., in the sauna test. 3–5 Volunteers were used per compound.

0.5 ml. of a 3% solution of the test compound was applied to a cleaned and precisely defined, circular skin area of about 5 cm$^2$ on the back. Transpiration was then initiated by thermal stimulation at 70° 14 80° C and about 10% relative air humidity. 10–20 minutes later, a filter paper impregnated with bromophenol blue was placed on the skin area under test and gently pressed for 10 seconds. In the presence of moisture, the paper becomes more or less strongly blue in color.

In order to be able to quantitatively determine the respective amount of perspiration secreted, "standard strengths" were first prepared: 5–40 mg. of water in appropriate amounts were added by means of a pipette to previously weighed sandpaper pieces (2 × 2 cm). The drops were finely distributed by means of a glass rod and the sandpaper pieces were subsequently re-weighed. One of the impregnated "bromophenol blue papers" was immediately placed on the weighed sandpaper and pressed for 10 seconds. Typical blue coloration standards were obtained for each amount of water chosen and these standards were compared with the color produced by the test compound.

Result:

I. 0–5 mg. of perspiration was secreted per 5 cm$^2$ after application of the following compounds:
Diethyl-aluminum-tert.butylate
Diisobutyl-aluminum-ethylate
Isobutyl-aluminum-diethylate
Diethyl-aluminum-cyclohexylate
Diethyl-aluminum-isopropylate
Diisobutyl-aluminum-n-propylate
Diisobutyl-aluminum-isobutylate
Diisobutyl-aluminum-n-butylate II. 5–10 mg of perspiration per 5 cm$^2$ were secreted after application of the following compounds:
Di(n-hexyl)-aluminum-2-phenoxyethylate
Diisobutyl-aluminum-2-phenoxyethylate
Diethyl-aluminum-2-phenoxyethylate
Diisobutyl-aluminum-phytylate
Isobutyl-aluminum-sesquiethylate
[[(CH$_3$)$_2$CHCH$_2$]$_{1.5}$Al(OC$_2$H$_5$)$_{1.5}$]
Diisobutyl-aluminum-geranylate
Diethyl-aluminum-(-)-menthylate
Diisobutyl-aluminum-phenylate
Di(n-octyl)-aluminum-ethylate
Diisobutyl-aluminum-undec-10-enoate
Di(n-hexyl)-aluminum-isopropylate
Diisobutyl-aluminum-n-butylate
Diethyl-aluminum-isobutylate
Diisobutyl-aluminum-cyclopentylate
Diisobutyl-aluminum-cyclohexylmethylate III. 10–15 mg. of prespiration per 5 cm$^2$ were secreted after application of the following compounds:
Diisobutyl-aluminum-n-hexadecylate
Diisobutyl-aluminum-d,l-α-tocopherylate/diisobutyl-aluminum-ethylate (molar ratio 1:1)
Ethyl-aluminum-diethylate
Ethyl-aluminum-diisopropylate
Isobutyl-aluminum-digeranylate
Diisobutyl-aluminum-(-)-menthylate
Diisobutyl-aluminum-tert.butylate
Diisobutyl-aluminum-acetate
Ethyl-aluminum-di(undec-10-enoate)
Diethyl-aluminum-undec-10-enoate
Ethyl-aluminum-di(2-phenoxyethylate)
Diisobutyl-aluminum-cyclohexylate
Diethyl-aluminum-benzylate
Diisobutyl-aluminum-benzylate
Di(n-hexyl)-aluminum-ethylate
Diisobutyl-aluminum-isopropylate
Diethyl-aluminum-n-propylate
Diethyl-aluminum-n-butylate
Diisobutyl-aluminum-methylate
Diethyl-aluminum-4-phenylphenylate
Ethyl-aluminum-mono-ethoxy-mono-n-propylate
Bis(diisobutyl-aluminum)-diethyleneglycolate
Diisobutyl-aluminum-isoamylate
Diethyl-aluminum-isoamylate
Diethyl-aluminum-p-tolylate
Bis(diethyl-aluminum)-diethyleneglycolate
Diisobutyl-aluminum-cyclopentylate
Diethyl-aluminum-cinnamylate
Diisobutyl-aluminum-2-methoxyethylate
Diisobutyl-aluminum-7-methoxy-3,7-dimethyl-octa-2-enylate IV. Untreated skin areas (placebo) secreted 40–50 mg. of perspiration.

The results indicate that the compounds listed under I, II and III showed antiperspiration activity with those under I having the greatest effect.

When the active compounds are incorporated into conventional cosmetically acceptable carriers, vehicles or formulations, then a composition with antiperspirant, deodorant or a combination of these properties is formed. Examples of carriers present in the antiperspirant and/or deodorant compositons of the present invention include the generally acceptable non-irritating carriers used for antiperspirants in cosmetics, e.g., in the form of powders, sticks, creams, solutions, aerosols and the like. Solvents for the active compounds which are cosmetically acceptable and compatible with conventional cosmetic additives are the anhydrous solvents mentioned above. The additives used are those for increasing the skin metabolism and/or the skin elasticity such as panthenol or one of its lower alkyl ethers, e.g., the ethyl ether, bactericidal substances, e.g., quaternary ammonium salts and/or perfumes. The compositions of this invention are preferably used in the form of aerosols containing the commonly used propellants such as low-boiling, liquified, chlorinated and fluorinated or unsubstituted alkanes, e.g., n-propane, n-butane, isobutane, n-hexane, dichlorodifluoromethane and dichlorotetrafluoroethane as well as mixtures thereof. A very usefl propellant mixture consists of about equal portions of dichlorodifluoromethane and dichlorotetrafluoroethane. The antiperspirant and/or deodorant compositions of the present invention preferably contain between about 1 and 30 percent by weight, more preferably between about 2 and 5 percent by weight of the active compound or mixtures of active compounds. Apart from the aforementioned additives, the present compositions can also contain other cosmetically valuable substances such as, for example, other perspiration-inhibiting or deodorizing compounds.

The novel compounds within the scope of formula Ic and the known compounds within the scope of formula I are prepared by analogous procedures, utilizing compounds with the substituents required to achieve the desired compound.

The following description is directed specifically to the preparation of the novel compounds within the scope of formula Ic.

The compounds within the scope of formula Ic are prepared by reacting a compound of the formula

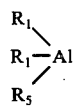

II wherein $R_1$ is an alkyl and $R_5$ is an alkyl, hydrogen, halogen or $-OR_{21}$, wherein $R_{21}$ has the same significance given above for $R_{20}$ except for formulas (a'), (a'') and (b') defined above, with an agent furnishing the group $-OR_{20}$, in which $R_{20}$ has the significance given above.

In accordance with the foregoing process, a group $-OR_{20}$ is introduced into the starting material of formula II. The reaction can be carried out according to known methods, for example, according to the following procedures.

Compounds within the scope of formula Ic in which $R_{20}$ is other than formula (a'), (a'') or (b') defined above can be prepared, for example, according to one of the following procedures (A)–(L):

$(R_1)_3Al + R_{21}OH \rightarrow (R_1)_2AlOR_{21} + R_1H$     (A)

$(R_1)_3Al + 2R_{21}OH \rightarrow R_1Al(OR_{21})_2 + 2R_1H$     (B)

$(R_1)_2AlH + R_{21}OH \rightarrow (R_1)_2AlOR_{21} + H_2$     (C)

$(R_1)_2AlH + 2R_{21}OH \rightarrow R_1Al(OR_{21})_2 + H_2 + R_1H$     (D)

$2(R_1)_2Al + Al(OR_{21})_3 \rightarrow 3(R_1)_2AlOR_{21}$     (E)

$(R_1)_3Al + 2Al(OR_{21})_3 \rightarrow 3R_1Al(OR_{21})_2$     (F)

$(R_1)_3Al + R_1Al(OR_{21})_2 \rightarrow 2(R_1)_2AlOR_{21}$     (G)

$2(R_1)_3Al + R_{21}OM \rightarrow (R_1)_2AlOR_{21} + MAl(R_1)_4$     (H)

$(R_1)_2AlHal + R_{21}OM \rightarrow (R_1)_2AlOR_{21} + MHal$     (J)

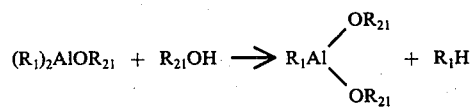

(K)

$(R_1)_2AlOR_{21} + Al(OR_{21})_3 \rightarrow 2R_1Al(OR_{21})_2$     (L)

In procedures (A)–(L), $R_1$ has the significance given above, $R_{21}$ has the same significance given above for $R_{20}$ except for formula (a'), (a'') or (b') as defined above. Hal is a halogen, preferably chlorine, and M is an alkali metal, preferably sodium or potassium.

Compounds within the scope of formula Ic in which $R_{20}$ is other than formula (a'), (a'') or (b') as defined above or a group bonded with the oxygen atom via carbonyl are prepared, for example, according to the following procedures (M)–(S):

$(R_{12})_3Al + R_{22}CHO \rightarrow (R_{12})_2AlOCH_2R_{22} + $ "$R_{12}$ $-\oplus$"     (M)

$(R_{12})_2AlH + R_{22}CHO \rightarrow (R_{12})_2AlOCH_2R_{22}$     (N)

$(R_{12})_3Al + (R_{23})_2CO \rightarrow (R_{12})_2AlOCH(R_{23})_2 + $ "$R_{12}$ $-\oplus$"     (O)

$(R_{12})_2AlH + (R_{23})_2CO \rightarrow (R_{12})_2AlOCH(R_{23})_2$     (P)

$(R_1)_2AlH + R_1CH(OR_{24})_2 \rightarrow (R_1)_2AlOR_{24} + R_1CH_2OR_{24}$     (Q)

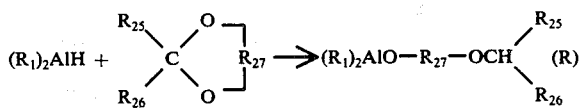

(R)

$2(R_1)_2AlH + R_{28}COOR_{24} \rightarrow (R_1)_2AlOCH_2R_{28} + (R_1)_2AlOR_{24}$     (S)

In procedures (M)–(S), $R_1$ has the significance given above, $R_{12}$ is an alkyl containing from 2 to 30 carbons, "$R_{12}$ $-\oplus$" is an alkene resulting from removal of a hydrogen atom from $R_{12}$. $-CH_2R_{22}$, $-CH(R_{23})_2$, $R_{24}$,

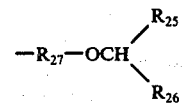

and $-CH_2R_{28}$ fall within the definition of $R_{20}$ but cannot represent formula (a'), (a'') or (b') or a group bonded with the oxygen atom via carbonyl.

Compounds within the scope of formula Ic in which $m$ is 2, $n$ is 1 and $R_{20}$ is formula (a') are prepared, for example, according to the following procedure (T):

$2(R_{10})_3Al + H_2O \rightarrow (R_{10})_2Al-O-Al(R_{10})_2 + 2R_{10}H$     (T)

In procedure (T), $R_{10}$ is an alkyl containing from 10 to 30 carbons.

Compounds within the scope of formula Ic in which $m$ is 2, $n$ is 1 and $R_{20}$ is formula (a'') are prepared, for example, according to the following procedure (U):

$2(R_{11})_3Al + HO-(R_3O)_{p'}-H \rightarrow (R_{11})_2AlO(R_3O)_{p'}$ $Al(R_{11})_2 + 2R_{11}H$     (U)

In procedure (U) above, $R_{11}$ is an alkyl containing from 2 to 30 carbons and $p'$ is 1 to 2.

Compounds within the scope of formula Ic in which $m$ is 1, $n$ is 2 and one of the $R_{20}$ symbols is an alkyl designated $R_{40}$ and the other is formula (b') are prepared, for example, according to the following procedure (V):

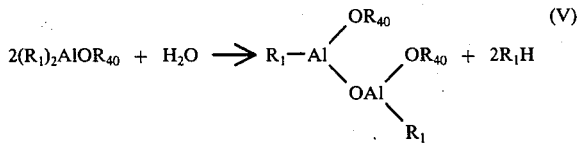

$$2(R_1)_2AlOR_{40} + H_2O \rightarrow R_1-Al\begin{pmatrix}OR_{40}\\OAl\begin{pmatrix}OR_{40}\\R_1\end{pmatrix}\end{pmatrix} + 2R_1H \quad (V)$$

In procedure (V), $R_1$ and $R_{40}$ are alkyls with $R_{40}$ containing from 3 to 30 carbons.

The reaction of a starting material within the scope of formula II with an agent furnishing the group $-OR_{20}$ as in procedures (A)-(V) in most cases proceeds almost quantitatively because of the high reactivity of the formula II starting materials. The quantitative ratio between the starting materials is not critical in procedures (F)-(J) and (L)-(S). In procedures (A)-(E), (K) and (T)-(V), the use of an excess of the second starting material above the stoichiometric molar ratio results in the introduction of an additional alkyl group ($R_1$, $R_{10}$, $R_{11}$) into the reaction product. Accordingly, the best yields of the products obtained according to procedures (A)-(E), (K) and (T)-(V) are obtained by maintaining substantially stoichiometric ratios between the reaction components. However, by varying the quantitative ratios of the reaction components above the stoichiometric ratios, mixtures of products falling within formula Ic are prepared. For example, by reaction $(R_1)_3Al$ or $(R_1)_2AlH$ with $R_{21}OH$ or $Al(OR_{21})_3$ while maintaining a molar ratio of the starting materials lying between that in procedures (A) and (B) or (C) and (D) or (E) and (F), a mixture of products are obtained. The mixture of products have the formulae $(R_1)_2AlOR_{21}$ and $R_1Al(OR_{21})_2$ and the mixture is represented by the formula $$(R_1)_{m'}Al(OR_{21})_{n'} \quad \text{I(d)}$$

wherein $R_1$ and $R_{21}$ have the significance given above and $m'$ and $n'$ each are a number which is greater than 1 but smaller than 2 and the sum of $m'$ and $n'$ is 3.
An example of a product of formula I(d) is

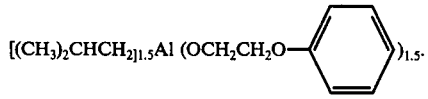

If the amount of the second starting material is greater than the stoichiometric molar ratio given in procedures (B), (D), (K) and (T)-(V), undesired products are obtained in addition to the desired products. For example, when 1 mole of $(R_1)_3Al$ or $(R_1)_2AlH$ is reacted with 2 to 3 moles of $R_{21}OH$ the desired product $R_1Al(OR_{21})_2$ is obtained in admixture with the undesired product $Al(OR_{21})_3$. The $Al(OR_{21})_3$ product can be separated from the desired product by conventional separation methods, e.g., fractional distillation.

It will be appreciated from the foregoing that it is not necessary to maintain the stoichiometric quantitative ratios of the starting components precisely in order to obtain a product falling within formula Ic. On the contrary, the quantitative ratios can be varied over a wide range.

Starting materials of formula II in which $R_5$ is hydrogen or halogen or an alkyl are strong reducing agents. When reacting such starting materials with readily reducible compounds, e.g., acids, esters, aldehydes or ketones, the reducible compound should be initially present in excess. The excess is provided by slowly adding the starting material to the reducible compound (and not vice-versa). By this means, an undesired reduction is substantially avoided.

The reaction of a starting material of formula II with an agent furnishing the group $-OR_{20}$ is preferably carried out in an inert organic solvent. Typical of such solvents are lower aliphatic or aromatic compounds unsubstituted or halogenated hydrocarbons such as n-hexane, n-heptane, methylene chloride, benzene, toluene or chlorobenzene or an ether such as diethyl ether, tetrahydrofuran or dioxane. The reaction temperature is not critical, but the reaction is preferably carried out in a temperature range lying between about $-50°$ C. and $+100°$ C.

The reaction of a starting material of formula II with an agent furnishing the group $-OR_{20}$ in most cases proceeds almost quantitatively. When pure starting materials are used, the desired product is obtained in practically pure form if an excess of the stoichiometric molar ratio is avoided. Purification is frequently unnecessary, namely when no undesired products result such as in procedures (E)-(G), (L), (N), (P), (R) and (S) or when the undesired product formed is a gas such as in procedure (C) and, when $R_1$ is a lower alkyl, also in procedures (A), (B), (D), (K), (M), (O) and (T)-(V). When purification of the product is desired, this can be carried out by conventional means, for example, by distillation.

The following Examples illustrate typical compositions and the preparation thereof provided by this invention. A mixture of 40% by volume dichlorodifluoromethane and 60% by volume dichlorotetrafluoroethane is used as the propellant gas mixture for the aerosols.

Example 1

| | | |
|---|---|---|
| a) | Diisobutyl-aluminum-ethylate | 3.0 g. |
| | n-Hexane | 7.0 g. |
| | Perfume | 0.1 g. |
| | Isobutyl myristate | 0.3 g. |
| | Propellant gas mixture | q.s. ad 100.0 g. |
| b) | Isobutyl-aluminum-diethylate | 3.0 g. |
| | n-Hexane | 7.0 g. |
| | Panthenol ethyl ether | 0.2 g. |
| | Propellant gas mixture | q.s. ad 100.0 g. |
| c) | Diisobutyl-aluminum-geranylate | 3.0 g. |
| | n-Hexane | 7.0 g. |
| | *Isopar Cosmetic® | 0.2 g. |
| | Propellant gas mixture | q.s. ad 100.0 g. |
| d) | Di(n-octyl)-aluminum-ethylate | 3.0 g. |
| | n-Hexane | 7.0 g. |
| | 6-Acetoxy-2,4-dimethyl-1,3-dioxane | 0.2 g. |
| | Propellant gas mixture | q.s. ad 100.0 g. |
| e) | Diisobutyl-aluminum(-)-menthylate | 3.0 g. |
| | n-Hexane | 7.0 g. |
| | Isopropyl myristate | 0.3 g. |
| | Propellant gas mixture | q.s. ad 100.0 g. |
| f) | Diisobutyl-aluminum-acetate | 3.0 g. |
| | n-Hexane | 7.0 g. |
| | Isopar Cosmetic® | 0.2 g. |
| | Propellant gas mixture | q.s. ad 100.0 g. |
| g) | Diisobutyl-aluminum-2-phenoxyethylate | 0.8 g. |
| | Diisobutyl-aluminum-ethylate | 1.2 g. |
| | Isobutyl-aluminum-diethylate | 1.0 g. |
| | n-Hexane | 7.0 g. |
| | Perfume | 0.3 g. |
| | Propellant gas mixture | q.s. ad 100.0 g. |
| h) | Diethyl-aluminum-cyclohexylate | 1.0 g. |
| | n-Hexane | 2.3 g. |
| | Isopar Cosmetic® | 9.0 g. |
| | Propellant gas mixture | q.s. ad 100.0 g. |
| i) | Diisobutyl-aluminum-ethylate | 2.5 g. |
| | Diethyl-aluminum-(-)-menthylate | 0.5 g. |
| | n-Hexane | 7.0 g. |
| | Propellant gas mixture | q.s. ad 100.0 g. |
| j) | Di(n-hexyl)-aluminum-2-phenoxyethylate | 1.0 g. |
| | Diethyl-aluminum-cyclohexylate | 2.0 g. |
| | n-Hexane | 7.0 g. |
| | Propellant gas mixture | q.s. ad 100.0 g. |
| k) | Di(n-hexyl)-aluminum-2-phenoxyethylate | 0.8 g. |
| | Diisobutyl-aluminum-ethylate | 1.2 g. |
| | Diethyl-aluminum-tert.butylate | 1.0 g. |

Example 1-continued

| | | |
|---|---|---|
| | n-Hexane | 7.0 g. |
| | Propellant gas mixture | q.s. ad 100.0 g. |
| l) | Di(n-hexyl)-aluminum-isopropylate | 3.0 g. |
| | n-Hexane | 7.0 g. |
| | Propellant gas mixture | q.d. 100.0 g. |
| m) | Diisobutyl-aluminum-2-phenoxyethylate | 3.0 g. |
| | n-Hexane | 7.0 g. |
| | Perfume | 0.3 g. |
| | Propellant gas mixture | q.s. ad 100.0 g. |
| n) | Di(n-hexyl)-aluminum-2-phenoxyethylate | 3.0 g. |
| | n-Hexane | 7.0 g. |
| | Propellant gas mixture | q.s. ad 100.0 g. |
| o) | Diethyl-aluminum-tert.butylate | 3.0 g. |
| | n-Hexane | 7.0 g. |
| | Propellant gas mixture | q.s. ad 100.0 g. |
| p) | Diethyl-aluminum-(-)-menthylate | 3.0 g. |
| | n-Hexane | 7.0 g. |
| | Propellant gas mixture | q.s. ad 100.0 g. |

*(Esso; aliphatic hydrocarbon containing principally 7 carbon atoms, used as solvent)

The active ingredient or mixtures of active ingredients are dissolved in the solvent and introduced into a suitable aerosol container while flushing with nitrogen. The remaining additives are added and the container is again flushed with nitrogen. The mixture is subsequently made up to 100 g. with the propellant gas mixture.

In the foregoing compositions, the active ingredients mentioned can be replaced by one or more of the compounds whose preparation is described in the following Examples 2 to 40. In these Examples, the products have been characterized by microanalyses (determination of the carbon, hydrogen and aluminum content; 1–2% error limit).

EXAMPLE 2

A solution of 13.8 g. (0.1 mol) of 2-phenoxyethanol in 100 ml. of n-heptane is added dropwise with intensive stirring within 20 minutes to a solution of 28.2 g. (0.1 mol) of tri(n-hexyl)-aluminum are dissolved in 180 ml. of n-heptane cooled to 0° C. The resulting mixture is stirred for 1 hour at room temperature and for a further hour at 30° C. Subsequently, the solvent is removed under reduced pressure. The last traces of n-heptane are removed by warming the resulting residue for 4 hours at 30° C./0.01 Torr. The resulting product, di(n-hexyl)-aluminum-2-phenoxyethylate, is obtained in pure form as a colorless liquid. This liquid solidifies to colorless crystals of melting point 46° C.

By the procedures of Example 2
diethyl-aluminum-n-hexadecylate (colorless liquid), is prepared from triethyl-aluminum and cetyl alcohol;

diisobutyl-aluminum-phytylate (slightly yellowish, viscous liquid) is prepared from triisobutyl-aluminum and phytol;

diisobutyl-aluminum-cyclohexylmethylate (colorless liquid) is prepared from triisobutyl-aluminum and cyclohexylmethyl alcohol;

diethyl-aluminum-cinnamylate (colorless, viscous liquid) is prepared from triethyl-aluminum and cinnamic alcohol;

diisobutyl-aluminum-cyclopentylate (white, semicrystalline mass) is prepared from triisobutyl-aluminum and cyclopentanol;

diethyl-aluminum-4-phenylphenylate (white crystals) is prepared from triethyl-aluminum and p-phenylphenol;

diisobutyl-aluminum-all-trans-retinylate (orange-red, resin-like material) is prepared from triisobutyl-aluminum and all-trans-vitamin A alcohol;

diethyl-aluminum-2-phenoxyethylate (fine, white needles) is prepared from triethyl-aluminum and 2-phenoxyethanol.

EXAMPLE 3

To 30 g. (0.1 mol) of all-trans-vitamin A acid in 300 ml. of absolute ether, cooled to −30° C. is added dropwise with intensive stirring within 1 hour a solution of 19.8 g. (0.1 mol) of triisobutyl-aluminum in 150 ml. of absolute ether. The resulting solution is slowly brought to 20° C. and stirred at this temperature for about 12 hours. Subsequently, the solvent is removed under reduced pressure. The resulting product, disobutyl-aluminum-1-all-trans-retinoate, is obtained in the form of gold-yellow crystals of melting point 200°–203° C. (decomposition).

By the procedures of Example 3
diisobutyl-aluminum-sorbate (slightly yellowish, honey-like liquid) is prepared from triisobutyl-aluminum and sorbic acid;

diisobutyl-aluminum-9-(4-methoxy-2,3,6-trimethyl-phenyl)-3,7-dimethyl-all-trans-nona-2,4,6,8-tetraenoate [orange-red crystals of melting point 148°–153° C. (decomposition)] is prepared from triisobutyl-aluminum and 9-(4-methoxy-2,3,6-trimethyl-phenyl)-3,7-dimethyl-all-trans-nona-2,4,6,8-tetraenoic acid;

diisobutyl-aluminum-geranoate (yellow, honey-like mass) is prepared from triisobutyl-aluminum and geranic acid.

EXAMPLE 4

To 36.8 g. (0.2 mol) of undec-10-enoic acid in 300 ml. of absolute ether cooled to −30° C. is added dropwise with intensive stirring within 1 hour a solution of 19.8 g. (0.1 mol) of triisobutyl-aluminum in 150 ml. of absolute ether. Subsequently, the resulting mixture is slowly brought to 20° C. and stirred at this temperature for 5 hours. The solvent is removed and the resulting residue freed from the residual solvent at 30° C./0.01 Torr for 4 hours. The resulting product, isobutyl-aluminum-di(undec-10-enoate), is obtained as a colorless semi-crystalline mass.

By the procedure of Example 4
isobutyl-aluminum-di(1-all-trans-retinoate) (yellow-brown crystals) is prepared from triisobutyl-aluminum and all-trans-vitamin A acid;

isobutyl-aluminum-disorbate (slightly yellowish crystals) is prepared from triisobutyl-aluminum and sorbic acid;

isobutyl-aluminum-di[9-(4-methoxy-2,3,6-trimethyl-phenyl)-3,7-dimethyl-all-trans-nona-2,4,6,8-tetraenoate] (yellow-brown crystals) is prepared from triisobutyl-aluminum and 9-(4-methoxy-2,3,6-trimethyl-phenyl)-3,7-dimethyl-all-trans-nona-2,4,6,8-tetraenoic acid;

isobutyl-aluminum-dicinnamoate [white powder of melting point 205° –208° C. (decomposition)] is prepared from triisobutyl-aluminum and cinnamic acid.

EXAMPLE 5

A solution of 43.0 g. (0.1 mol) of d,l-α-tocopherol in 100 ml. of n-heptane is added dropwise while stirring to a soluton of 14.2 g. (0.1 mol) of diisobutyl-aluminum hydride in 100 ml. of absolute n-heptane cooled to 0° C. The resulting mixture is stirred for 10 hours at room temperature and subsequently for 2 hours at 40° C. The solvent is removed by distillation under reduced pressure. The resulting product, diisobutyl-aluminum-d,1-α-tocopherylate, is obtained as a honey-yellow, syrupy mass, which has good solubility in hydrocarbons, ethers and esters.

EXAMPLE 6

14.2 g. (0.1 mol) of diisobutyl-aluminum hydride and 27.6 g. (0.2 mol) of 2-phenoxyethanol are reacted together by the process described in Example 5. The process is modified because 2-phenoxyethanol is immiscible with n-heptane. Accordingly, 2-phenoxyethanol is emulsified with the n-heptane by magnetic stirring in a dropping funnel before adding dropwise to the diisobutyl-aluminum hydride. The remaining procedure is as in Example 5.

The resulting isobutyl-aluminum-di(2-phenoxyethylate) is a colorless, resinous mass.

EXAMPLE 7

19.8 g. (0.1 mol) of triisobutyl-aluminum in 300 ml. of absolute n-hexane are treated dropwise within 0.5 hour at 0° C. with a solution of 15.2 g. (0.1 mol) of citral in 200 ml. of absolute n-hexane. The resulting mixture is left to stand for 1 hour at 20° C. and subsequently for 1 hour at 60° C. The solvent is then removed at 30° C./0.01 Torr for 4 hours. The resulting product, diisobutyl-aluminum-3,7-dimethyl-octa-2,6-dienylate, is obtained as a slightly yellowish colored, viscous liquid.

EXAMPLE 8

Equimolar amounts of diisobutyl-aluminum hydride and 7-methoxy-3,7-dimethyl-octa-2-en-1-al are reacted together by the process described in Example 7. The resulting diisobutyl-aluminum-7-methoxy-3,7-dimethyl octa-2-enylate is a slightly yellowish, viscous liquid and is a mixture of the geometric isomers (7-methoxy-geranylate/7-methoxy-nerolylate).

EXAMPLE 9

14.2 g. (0.1 mol) of diisobutyl-aluminum hydride and 14.2 g. (0.1 mol) of cyclohexanone ethylene ketal in 100 ml. of absolute toluene are held at 80° C. for 12 hours. The solvent is distilled off under reduced pressure at 25° C/0.01 Torr for 4 hours. The resulting product, diisobutyl-aluminum-2-cyclohexyloxyethylate, is obtained as a colorless, viscous liquid.

EXAMPLE 10

A solution of 39.6 g (0.2 mol) of triisobutyl-aluminum in 200 ml. of absolute n-hexane is added dropwise within 1 hour at 0° C. to 10.6 g. (0.1 mol) of diethylene glycol in 250 ml. of absolute n-hexane. The resulting mixture is stirred for 1 hour at room temperature and subsequently for 1 hour at 40° C. The solvent is removed at 30° C./0.01 Torr for 4 hours. The resulting product, bis(diisobutyl-aluminum)-diethyleneglycolate, is a colorless, strongly viscous liquid.

By the process of Example 10
bis(diethyl-aluminum)-diethyleneglycolate (colorless, semi-crystalline, honey-like mass) is prepared from triethyl-aluminum and diethylene glycol;

bis(diisobutyl-aluminum)-ethyleneglycolate (colorless, honey-like/wax-like mass) is prepared from triisobutyl-aluminum and ethylene glycol.

EXAMPLE 11

An emulsion of 13.8 g. (0.1 mol) of 2-phenoxyethanol in 50 ml. of absolute n-hexane is added dropwise with stirring to 27.8 g. (0.1 mol) of diisobutyl-aluminum-2-phenoxyethylate in 100 ml. of absolute n-hexane. The resulting mixture is stirred for 1 hour at room temperature and for 1 hour under reflux conditions. Subsequently, the solvent is removed and the resulting residue held at 30° C./0.01 Torr for 4 hours. The resulting product, isobutyl-aluminum-di(2-phenoxyethylate), is obtained as a colorless, resinous mass.

Following the procedures of Example 11
isobutyl-aluminum-diphytylate (orange-colored, honey-like mass) is prepared from diisobutyl-aluminum-phytylate and phytol;

isobutyl-aluminum-digeranylate (yellow-red liquid) is prepared from diisobutyl-aluminum-geranylate and geraniol;

ethyl-aluminum-di(2-phenoxyethylate) (white crystals) is prepared from diethyl-aluminum-2-phenoxyethylate and 2-phenoxyethanol.

EXAMPLE 12

A suspension of 27.6 g. (0.2 mol) of pheoxyethanol in 150 ml. of absolute n-hexane is added dropwise at 0° C. with stirring to 19.8 g. (0.1 mol) of triisobutyl-aluminum in 250 ml. of absolute n-hexane. The resulting mixture is stirred for 12 hours at 20° C. and for 1 hour at 40° C. Subsequently, the solvent is removed and the resulting residue held at 30° C./0.01 Torr for 4 hours. The product, isobutyl-aluminum-di(2-phenoxyethylate) is thereby obtained.

Following the procedures of Example 12 k
isobutyl-aluminum-diphytylate (orange-colored, honey-like mass) is prepared from triisobutyl-aluminum and phytol;

isobutyl-aluminum-digeranylate (yellow-red liquid) is prepared from triisobutyl-aluminum and geraniol;

ethyl-aluminum-di(2-phenoxyethylate) (white crystals) is prepared from triethyl-aluminum and 2-phenoxyethanol.

EXAMPLE 13

To 11.4 g. (0.1 mol) of triethyl-aluminum in 100 ml. of absolute n-heptane are added dropwise at 0° C. while stirring, initially a solution of 12.8 g. (0.1 mol) of 2-cyclohexyl-ethanol in 50 ml. of n-heptane and then a solution of 13.8 g. (0.1 mol) of 2-phenoxyethanol in 50 ml. of n-heptane. The resulting mixture is stirred for 10 hours at room temperature and subsequently for 2 hours at 40° C. The solvent is evaporated under reduced pressure. The product, ethyl-aluminum-2-cyclohexylethylate-2-phenoxyethylate, is thereby obtained.

EXAMPLE 14

Equimolar amounts of triisobutyl-aluminum and cyclopentanone are reacted together by the procedure described in Example 7. The product, diisobutyl-aluminum-cyclopentylate, is thereby obtained as a colorless liquid.

EXAMPLE 15

Following the procedure described in Example 7, equimolar amounts of diisobutyl-aluminum hydride and cyclopentanone are reacted to obtain diisobutyl-aluminum-cyclopentylte as a colorless liquid.

EXAMPLE 16

28.4 g. (0.2 mol) of diisobutyl-aluminum hydride are reacted with 16.6 g. (0.1 mol) of 3-phenoxyacetic acid methyl ester by the procedure described in Example 7. A mixture of diisobutyl-aluminum-2-phenoxyethylate amd diisobutyl-aluminum-methylate in a ratio of 1:1 is thereby obtained.

EXAMPLE 17

36.6 g. (0.1 mol) of aluminum-tricyclohexylmethylate and 22.8 g. (0.1 mol) of triethyl-aluminum are heated together at 90° C. for 3 hours. The product, diethyl-aluminum-cyclohexylmethylate, is thereby obtained.

EXAMPLE 18

Following the procedure described in Example 17, 73.2 g. (0.2 mol) of aluminum-tricyclohexylmethylate and 11.4 g. (0.1 mol) of triethyl-aluminum are reacted to obtain ethyl-aluminum-dicyclohexylmethylate.

EXAMPLE 19

Following the procedure described in Example 17, 18.8 g. (0.1 mol) of diethyl-aluminum-cyclohexylmethylate and 36.6 g. (0.1 mol) of aluminum-tricyclohexylmethylate are reacted to obtain ethyl-aluminum-ditricyclohexylmethylate.

EXAMPLE 20

49.5 g. (0.28 mol) of diisobutyl-aluminum chloride are added dropwise within 30 minutes with stirring to a suspension of 63.0 g. (0.31 mol) of anhydrous sodium undec-10-enoate in 100 ml. of pentane. The resulting mixture is left to stand for 6 hours and then the sodium chloride which is formed is centrifuged off. After evaporation of the solvent under atmospheric pressure and subsequently at about 15 Torr, diisobutyl-aluminum-undec-10-enoate is obtained.

EXAMPLE 21

0.36 g. (14.5 mmol) of water are added dropwise to 36.5 g. (46.5 mmol) of trioctadecyl-aluminum in a nitrogen atmosphere. After 18 hours at $-40°$ C., the mixture is warmed to room temperature to obtain (n-octadecyl)-dialuminum oxane.

EXAMPLE 22

A sealed vessel (equipped with a side-tube) containing 12 mmol of diisobutyl-aluminum-2-phenoxyethylate in 100 ml. of benzene as well as (in the side-tube) 6 mmol of water, is immersed in liquid nitrogen. The vessel is placed under reduced pressure and slowly warmed to room temperature. The benzene solution is held at about 5° C. while the side-tube is slowly warmed, whereby water flows into the benzene solution. After uptake of the water, the solvent is removed. The product, bis(isobutyl-2-phenoxyethoxy-aluminum)oxane, is thereby obtained.

EXAMPLE 23

50.2 g. of diisobutyl-aluminum hydride are added dropwise while stirring at 10° $-20°$ C. to 100 g. of d,l-α-tocopherol in 500 ml. of pentane. After termination of the gas evolution, the mixture is stirred for a further 3 hours at room temperature and the pentane is removed under reduced pressure. The product, diisobutyl-aluminum-d,1-α-tocopherylate, is obtained as a viscous, yellow residue.

EXAMPLE 24

By replacing the d,1-α-tocopherol in Example 23 with d,1-α-tocopheryl acetate, a mixture of diisobutyl-aluminum-d,1-α-tocopherylate and diisobutyl-aluminum-ethylate in a molar ratio of 1:1 is obtained.

EXAMPLE 25

A solution of 4.6 g. (0.1 mol) of ethanol in 50 ml. of absolute n-hexane is added dropwise within 0.5 hour with stirring at 0° C. to 19.8 g. (0.1 mol) of triisobutyl-aluminum in 250 ml. of absolute n-hexane at 0° C. The resulting mixture is subsequently stirred for 1 hour at 40° C. The solvent is removed and the resulting residue distilled under reduced pressure to obtain diisobutyl-aluminum-ethylate as a colorless liquid which boils at 122° C./1.5 mm.

EXAMPLE 26

Following the procedure described in Example 2, diethyl-aluminum-p-tolylate (colorless liquid) is prepared from triethyl-aluminum and p-cresol;

di(n-octadecyl)aluminum-benzylate (colorless, vitreous mass) is prepared from tri(n-octadecyl)-aluminum and benzyl alcohol.

diethyl-aluminum-tert.butylate is prepared from triethyl-aluminum and tert .butanol;

diethyl-aluminum-cyclohexylate is prepared from triethyl-aluminum and cyclohexanol;

di(n-octyl)-aluminum-ethylate is prepared from tri)n-octyl)-aluminum and ethnaol; and di(n-hexyl)-aluminum-isopropylate is prepared from tri(n-hexyl)-aluminum and isopropanol.

EXAMPLE 27

A solution of 4.6 g. (0.1 mol) of absolute ethanol in 50 ml. of absolute n-hexane is added dropwise with stirring to 13 g. (0.1 mol) of diethyl-aluminum-ethylate in 100 ml. of absolute n-hexane. The resulting mixture is stirred for 1 hour at room temperature and for 1 hour under reflux conditions. The solvent is subsequently removed and its last residues are removed at 30° C./0.01 Torr for 4 hours. The resulting ethyl-aluminum-diethylate is a viscous, colorless liquid which boils at 137° C./0.1 mm.

EXAMPLE 28

A solution of 12.02 g. (0.2 mol) of absolute isopropanol in 150 ml. of absolute n-hexane is added dropwise while stirring at 0° C. to 11.4 g. (0.1 mol) of triethyl-aluminum in 250 ml. of absolute n-hexane. The mixture is stirred for 12 hours at 20° C. and for 1 hour at 40° C. Subsequently, the solvent is evaporated under reduced pressure and the residue is freed from traces of solvent by warming at 30° C./0.01 Torr. for 4 hours to obtain ethyl-aluminum-diisopropylate as a colorless, viscous liquid.

Following the procedure of Example 28, isobutyl-aluminum-diethylate is prepared from triisobutyl-aluminum and ethanol.

EXAMPLE 29

To 11.4 g. (0.1 mol) of triethyl-aluminum in 100 ml. of absolute n-heptane cooled to 0° C. are added dropwise with stirring, a solution of 6 g. (0.1 mol) of n-propanol in 50 ml. of n-heptane followed by the addition of a solution of 4.6 g. (0.1 mol) of the ethanol in 50 ml. of n-heptane. The resulting mixture is stirred for 10 hours at room temperature and for 2 hours at 40° C. After removal of the solvent under reduced pressure, ethyl-aluminum-ethylate-n-propylate, is obtained as a colorless liquid.

EXAMPLE 30

Following the procedure described in Example 7, diisobutyl-aluminum-isopropylate is obtained as a colorless liquid by reacting equimolar amounts of triisobutyl-aluminum and acetone.

EXAMPLE 31

Following the procedure described in Example 7, diisobutyl-aluminum-cyclohexylate is obtained as a colorless, viscous liquid by reacting equimolar amounts of diisobutyl-aluminum hydride and cyclohexanone.

EXAMPLE 32

14.2 g. (0.1 mol) of diisobutyl-aluminum hydride and 14.6 g. (0.1 mol) of 1,1-diethoxybutane in 100 ml. of absolute toluene are heated for 20 hours at 80° C. The n-butyl ethyl ether formed in the reaction and the toluene are removed under reduced pressure and the residue is subsequently held at 35° C./0.01 Torr for 4 hours. The resulting product, diisobutyl-aluminum-ethylate, boils at 123° C./2 mm.

EXAMPLE 33

Following the procedure described in Example 7, 28.4 g. (0.2 mol) of diisobutyl-aluminum hydride are reacted with 8.8 g. (0.1 mol) of ethyl acetate to produce diisobutyl-aluminum-ethylate.

EXAMPLE 34

16.2 g. (0.1 mol) of aluminum-triethylate and 22.8 g. (0.2 mol) of triethyl-aluminum are heated together for 3 hours at 90° C. After distillation under reduced pressure, diethyl-aluminum-ethylate is obtained.

EXAMPLE 35

32.4 g. (0.2 mol) of aluminum-triethylate and 11.4 g. (0.1 mol) of triethyl-aluminum are heated together for 3 hours at 90° c. after distillation under reduced pressure, ethyl-aluminum-diethylate is obtained.

EXAMPLE 36

13 g. (0.1 mol) of diethyl-aluminum-ethylate and 16.2 g. (0.1 mol) of aluminum-ethylate are heated together for 3 hours at 90° C. After distillation under reduced pressure ethyl-aluminum-diethylate is obtained.

EXAMPLE 37

49.5 g. (0.28 mol) of diisobutyl-aluminum-chloride are added dropwise within 30 minutes with stirring to a suspension of 25.5 g. (0.31 mol) of anhydrous sodium acetate in 100 ml. of pentane. The resulting mixture is left to stand for 6 hours and the sodium chloride formed is subsequently centrifuged off. After evaporation of the solvent under atmospheric pressure and subsequently at about 15 Torr, diisobutyl-aluminum-acetate is obtained.

EXAMPLE 38

0.26 g. (14.5 mol) of water are added dropwise in a nitrogen atmosphere to 5.32 g. (46.5 mmol) of triethyl-aluminum. After 18 hours at −40° C., the resulting mixture is distilled under reduced pressure in order to remove the triethyl-aluminum to obtain tetraethyl-dialuminum-oxane.

EXAMPLE 39

A sealed vessel (equipped with a side-tube) containing 12 mmol of diethyl-aluminum-ethylate in 100 ml. of benzene as well as (in the side-tube) 6 mmol of water, is immersed in liquid nitrogen. The vessel is placed under reduced pressure and slowly warmed to room temperature. The benzene solution is held at about 5° C. while the side-tube is slowly warmed, whereby water flows into the benzene solution. After uptake of the water, the solvent is removed to obtain bis(ethyl-ethoxy-aluminum)-oxane.

EXAMPLE 40

1.8 g. (0.1 mol) of triisobutyl-aluminum are added under an inert gas atmosphere to 35.8 g. (0.1 mol) of isobutyl-aluminum-di(2-phenoxyethylate). The resulting mixture is heated at 95°–100° C. for 4 hours while stirring. After cooling, the mass obtained solidifies. The thus-obtained colorless diisobutyl-aluminum-2-phenoxyethylate melts at 68°–70° C.

We claim:

1. An antiperspirant/deodorant composition which contains (a) a compatible cosmetically acceptable aerosol propellant and (b) as the active ingredient 1% to 30% by weight of one or a mixture of compounds represented by the formula $$(R_1)_m Al(OR_2)_n \qquad \text{I}$$

wherein $m$ and $n$ each are 1 or 2 and the sum of $m$ and $n$ is 3; $R_1$ is alkyl containing from 2 to 30 carbon atoms; $R_2$ is subsituted and unsubstituted radicals selected from the group consisting of alkyl containing from 1 to 20 carbon atoms, cycloalkyl containing 5 or 6 carbon atoms, alkenyl containing from 1 to 20 carbon atoms, cycloalkenyl containing 5 to 6 carbon atoms, aryl having 1 or 2 aromatic nuclei, alkanoyl containing from 20 to 30 carbon atoms, alkenoyl containing from 2 to 30 carbon atoms and aroyl having 1 to 2 aromatic nuclei; wherein the substituents on $R_2$ when $R_2$ is selected from the grouo consisting of alkyl, alkenyl, alkanoyl and alkenoyl and mixtures thereof are one or more of cycloalkyl containing 5 or 6 carbon atoms, cycloalkenyl containing 5 or 6 carbon atoms substituted cycloalkenyl containing 5 or 6 carbon atoms, aryl containing 1 or 2 aromatic nuclei, alkoxy containing 1 to 20 carbon atoms, cycloalkoxy containing 5 or 6 carbon atoms, cycloalkenyloxy contaning 5 or 6 carbon atoms, aryloxy containing 1 or 2 aromatic nuclei, alkyl containing 1 to 20 carbon atoms and alkoxy containing 1 to 20 carbon atoms and mixture thereof, substituted aryl containing 1 or 2 aromatic nuclei, cycloalkenyloxy containing 5 or 6 carbon atoms or aryloxy containing 1 or 2 aromatic nuclei; and wherein the substitutents on $R_2$ when $R_2$ is the said cycloalkyl, cycloalkenyl, aryl and aroyl groups are one or more of alkyl containing 1 to 20 carbon atoms, alkoxy containing 1 to 20 carbon atoms or aryl containing 1 or 2 aromatic nuclei; and when $R_2$ is phenyl, two adjacent alkyl and alkoxy substituents and mixture thereof on the phenyl can be joined to form a 5- or 6-membered saturated ring; when $m$ is 2 and $n$ is 1, $R_2$ can be $$-(R_3O)_p-Al(R_1)_2 \qquad \text{(a)}$$

wherein $R_1$ has the significance above and each $R_1$ can be the same or different, $R_3$ is a straight chain alkylene of 2 to 4 carbons and $p$ is 0, 1 or 2; when $m$ is 1 and $n$ is 2, $R_2$ has the significance above and each $R_2$ can be the same or different or when one $R_2$ is alkyl the other $R_2$ can be

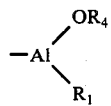

wherein $R_1$ has the significance above and $R_4$ is alkyl containing 1 to 20 carbon atoms.

2. An antiperspirant/deodorant composition according to claim 6 which contains as the active ingredient one or a mixture of compounds according to claim 1 in which $R_2$ is an alkyl substituted by cycloalkyl, cycloalkoxy or aryloxy; an alkenyl substituted by alkyl substituted cycloalkenyl or alkoxy; an alkenoyl substituted by alkyl-substituted cycloalkenyl or by an aryl radical substituted by an alkyl radical, an alkoxy radical or mixtures thereof; or an alkyl-substituted chromanyl.

3. An antiperspirant/deodorant composition which contains (a) a compatible cosmetically acceptable aerosok propellant and (b) as the active ingredient 1% to 30% by weight of one or a mixture of compounds according to claim 1 in which $R_1$ is an alkyl containing 2 to 8 carbons and $R_2$ is alkyl containing from 1 to 8 carbons, a phenoxy substituted alkyl containing 1 to 8 carbons in the alkyl, cyclohexyl o cyclohexyl substituted by alkyl containing from 1 to 4 carbons.

4. An antiperspirant/deodorant composition according to claim 3 wherein the active ingredient is diisobutyl-aluminum-2-phenoxyethylate.

5. An antiperspirant/deodorant composition according to claim 3 wherein the active inredient is di(n-n-hexyl)-aluminum-2-phenoxylate.

6. An antiperspirant/deodorant composition according to claim 3 wherein the active ingredient is diethylaluminym-tert.butylate.

7. An antiperspirant/deodorant composition according to claim 3 wherein the active ingredient is diisobutyl-aluminum-ethylate.

8. An antiperspirant/deodorant composition according to claim 3 wherein the active ingredient is isobutylaluminum-diethylate.

9. An antiperspirant/deodorant composition according to claim 3 wherein the active ingredient is diethylaluminum-cyclohexylate.

10. An antiperspirant/deodorant composition according to claim 3 wherein the active ingredients is diethylaluminum-menthylate.

11. An antiperspirant/deodorant composition according to claim 3 wherein the active ingredients is di(n-octyl)-aluminum-ethylate.

12. An antiperspirant/deodorant composition according to claim 3 wherein the active ingredient is di(n-hexyl)-aluminum-isopropylate.

13. A method of controlling perspiration and perspiration odor comprising applying to the skin area to be affected, the composition of claim 1.

14. A method of controlling perspiration and perspiration odor comprising applying to the skin are to be affected, the composition claim 3.